(12) United States Patent
Tanaka et al.

(10) Patent No.: US 6,482,412 B1
(45) Date of Patent: Nov. 19, 2002

(54) POLYPEPTIDE HAVING HUMAN HIV INHIBITORY ACTIVITY, A GENE ENCODING THE POLYPEPTIDE, A METHOD TO PRODUCE THE POLYPEPTIDE

(75) Inventors: Haruo Tanaka, Machida (JP); Satoshi Ohmura, Tokyo (JP)

(73) Assignees: Gakkou Houjin Kitasato Gakuen, Tokyo (JP); Japan Society for the Promotion of Science, Tokyo (JP)

( * ) Notice: Subject to any disclaimer, the term of this patent is extended or adjusted under 35 U.S.C. 154(b) by 0 days.

(21) Appl. No.: 09/674,608
(22) PCT Filed: Sep. 22, 1999
(86) PCT No.: PCT/JP99/05199

§ 371 (c)(1),
(2), (4) Date: Jan. 24, 2001

(87) PCT Pub. No.: WO00/52043

PCT Pub. Date: Sep. 8, 2000

(30) Foreign Application Priority Data

Mar. 4, 1999 (JP) ............................................. 11-056960
Mar. 5, 1999 (JP) ............................................. 11-058434

(51) Int. Cl.$^7$ ........................ A61K 39/00; A61K 39/21; C12P 21/04

(52) U.S. Cl. ................................ 424/185.1; 424/184.1; 424/188.1; 424/246.1; 435/70.1

(58) Field of Search ........................... 424/184.1, 185.1, 424/188.1, 246.1; 435/70.1

(56) References Cited

FOREIGN PATENT DOCUMENTS

JP          7-508746          9/1995

OTHER PUBLICATIONS

Tanaka et al., *The Journal of Antibiotics*, 50(1):58–65 (1997).
Matsuzaki et al., *The Journal of Antibiotics*, 50(1):66–69 (1997).

*Primary Examiner*—Hankyel T. Park
*Assistant Examiner*—Stacy S. Brown
(74) *Attorney, Agent, or Firm*—Burns Doane Swecker & Mathis LLP

(57) ABSTRACT

A novel compound, which is effective for treatment of AIDS and has inhibitory activity on human immunodeficiency viruses (HIV), was examined. The K97-0003 peptide, which has anti-HIV activity caused by inhibition of syncytium formation by fusion of envelope glycoprotein of HIV and the host cells expressing the receptor to said virus, was provided by the present invention. Furthermore, the base sequence of the gene coding for said polypeptide, and the method for preparing said polypeptide using strain K97-0003 were provided.

9 Claims, 4 Drawing Sheets

SEQUENCE LISTING

```
<160> NUMBER OF SEQ ID NOS: 10

<210> SEQ ID NO 1
<211> LENGTH: 114
<212> TYPE: PRT
<213> ORGANISM: Actinomyces K97-0003 Strain

<400> SEQUENCE: 1

Ala Ser Val Thr Ile Arg Asn Ala Gln Thr Gly Arg Leu Leu Asp Ser
1               5                   10                  15

Asn Tyr Asn Gly Asn Val Tyr Thr Leu Pro Ala Asn Gly Gly Asn Tyr
            20                  25                  30

Gln Arg Trp Thr Gly Pro Gly Asp Gly Thr Val Arg Asn Ala Gln Thr
        35                  40                  45

Gly Arg Cys Leu Asp Ser Asn Tyr Asp Gly Ala Val Tyr Thr Leu Pro
    50                  55                  60

Cys Asn Gly Gly Ser Tyr Gln Lys Trp Leu Phe Tyr Ser Asn Gly Tyr
65                  70                  75                  80

Ile Gln Asn Val Glu Thr Gly Arg Val Leu Asp Ser Asn Tyr Asn Gly
                85                  90                  95

Asn Val Tyr Thr Leu Pro Ala Asn Gly Gly Asn Tyr Gln Lys Trp Tyr
            100                 105                 110

Thr Gly

<210> SEQ ID NO 2
<211> LENGTH: 160
<212> TYPE: PRT
<213> ORGANISM: Actinomyces K97-0003 Strain

<400> SEQUENCE: 2

Met Asn Thr Leu Thr Lys Leu Thr Ile Gly Ala Val Ala Leu Thr Gly
1               5                   10                  15

Ser Phe Leu Ala Ala Ala Pro Ala Ser Ala Ala Pro Ala Ala Asp Thr
            20                  25                  30

Thr Ala Ser Pro Ala Leu Gly Ser Gln Val Ser Ala Gln Phe Ala Ser
        35                  40                  45

Val Thr Ile Arg Asn Ala Gln Thr Gly Arg Leu Leu Asp Ser Asn Tyr
    50                  55                  60

Asn Gly Asn Val Tyr Thr Leu Pro Ala Asn Gly Gly Asn Tyr Gln Arg
65                  70                  75                  80

Trp Thr Gly Pro Gly Asp Gly Thr Val Arg Asn Ala Gln Thr Gly Arg
                85                  90                  95

Cys Leu Asp Ser Asn Tyr Asp Gly Ala Val Tyr Thr Leu Pro Cys Asn
            100                 105                 110

Gly Gly Ser Tyr Gln Lys Trp Leu Phe Tyr Ser Asn Gly Tyr Ile Gln
        115                 120                 125
```

```
Asn Val Glu Thr Gly Arg Val Leu Asp Ser Asn Tyr Asn Gly Asn Val
    130                 135                 140

Tyr Thr Leu Pro Ala Asn Gly Gly Asn Tyr Gln Lys Trp Tyr Thr Gly
145                 150                 155                 160
```

<210> SEQ ID NO 3
<211> LENGTH: 342
<212> TYPE: DNA
<213> ORGANISM: Actinomyces K97-0003 Strain

<400> SEQUENCE: 3

```
gcctcggtga ccatccgcaa cgcccagacc ggccgcctgc tggacagcaa ctacaacggc      60
aacgtctaca cgctgcccgc caacggcggg aactaccagc ggtggaccgg ccccggcgac     120
ggcaccgtcc gcaacgccca gaccggccgc tgcctcgaca gcaactacga cggcgccgtc     180
tacacgctgc cgtgcaacgg cggtagctac agaagtggc tgttctacag caacggctac      240
atccagaacg tcgagaccgg acgcgtgctc gacagcaact acaacggcaa cgtgtacaca     300
ctgccggcca acggcggcaa ctaccagaag tggtacaccg gc                         342
```

<210> SEQ ID NO 4
<211> LENGTH: 480
<212> TYPE: DNA
<213> ORGANISM: Actinomyces K97-0003 Strain

<400> SEQUENCE: 4

```
atgaataccc tgaccaagct caccatcgga gccgtcgccc tgacgggctc gttcctggcc      60
gccgccccgg cctccgcggc acccgccgcc gacaccaccg ccagcccggc tctgggctcg     120
caggtctccg cccagttcgc ctcggtgacc atccgcaacg cccagaccgg ccgcctgctg     180
gacagcaact acaacggcaa cgtctacacg ctgcccgcca acggcgggaa ctaccagcgg     240
tggaccggcc ccggcgacgg caccgtccgc aacgcccaga ccggccgctg cctcgacagc     300
aactacgacg gcgccgtcta cacgctgccg tgcaacggcg gtagctacca gaagtggctg     360
ttctacagca acggctacat ccagaacgtc gagaccggac gcgtgctcga cagcaactac     420
aacggcaacg tgtacacact gccggccaac ggcggcaact accagaagtg gtacaccggc     480
```

<210> SEQ ID NO 5
<211> LENGTH: 7
<212> TYPE: PRT
<213> ORGANISM: Actinomyces K97-0003 Strain

<400> SEQUENCE: 5

```
Ala Ser Val Thr Ile Arg Asn
1               5
```

<210> SEQ ID NO 6
<211> LENGTH: 6
<212> TYPE: PRT
<213> ORGANISM: Actinomyces K97-0003 Strain

<400> SEQUENCE: 6

```
Gln Lys Trp Tyr Thr Gly
1               5
```

<210> SEQ ID NO 7
<211> LENGTH: 21
<212> TYPE: DNA
<213> ORGANISM: Actinomyces K97-0003 Strain

<400> SEQUENCE: 7

-continued

```
gcstcsgtsa csatccgsaa c                                        21

<210> SEQ ID NO 8
<211> LENGTH: 17
<212> TYPE: DNA
<213> ORGANISM: Actinomyces K97-0003 Strain

<400> SEQUENCE: 8
ccsgtgtacc acttctg                                             17

<210> SEQ ID NO 9
<211> LENGTH: 18
<212> TYPE: DNA
<213> ORGANISM: Actinomyces K97-0003 Strain

<400> SEQUENCE: 9
gcctcggtga ccatccgc                                            18

<210> SEQ ID NO 10
<211> LENGTH: 15
<212> TYPE: DNA
<213> ORGANISM: Actinomyces K97-0003 Strain

<400> SEQUENCE: 10
gtcgagcacg cgtcc                                               15
```

POLYPEPTIDE HAVING HUMAN HIV INHIBITORY ACTIVITY, A GENE ENCODING THE POLYPEPTIDE, A METHOD TO PRODUCE THE POLYPEPTIDE

This application claims priority to Japanese Patent Application Number 11-56,960, filed Mar. 4, 1999, and to Japanese Patent Application Number 11-58,434, filed Mar. 5, 1999.

BACKGROUND OF THE INVENTION

1. Field of the Invention

This invention relates to an anti-viral agent useful for treatment of infectious disease caused by human immunodeficiency viruses (HIV). In particular, it relates to a polypeptide which can inhibit HIV-1 infectious disease, a DNA coding for said polypeptide, and a process for producing said polypeptide.

2. Description of the Related Art

Currently, reverse transcriptase inhibitors and protease inhibitors are used for medical treatment of acquired immune deficiency syndrome (AIDS) caused by HIV-1 virus. As for the reverse transcriptase inhibitors, nucleoside type compounds such as zidovudine (AZT, 3'-azido-2',3'-dideoxycyltidine), didanosine (ddI, 2',3'-dideoxyinosine), zalcitabin (ddC, 2',3'-dideoxycytidine), sutavudine (d4T, 2',3'-dideoxy-2',3'-didehydrothymidine) and lamivudine (3TC,3'-thiacytidine), or non-nucleoside compounds such as nevirapine, are used.

Concerning nucleoside type reverse transcriptase inhibitors, it is known that resistant strains will appear within about one year after administration of the inhibitors and some serious side effects are caused by chronic administration. On the other hand, side effects are rarely caused by administration of non-nucleoside type reverse transcriptase inhibitors, resistant strains tend to appear in early stages of an administration, because of high specificity of these inhibitors. Nowadays, saquinavir, ritonavir, indinavir and the like are used for protease inhibitors. Although these protease inhibitors exhibit considerable anti-viral activity by single administration, in general the effect remains to be only transient. The sensitivity of HIV strains tends to decrease by mutation of the amino acid sequence of HIV proteases. In addition, there are problems in respect to stability in living body and occurrence of side effects such as disorder on digestive organ.

Recently, the U.S. AIDS Clinical Trials Group reported that the combination therapy using AZT and ddI, or AZT and ddC brought better results in three indexes described below, compared with the monotherapy using AZT alone, which have been recognized to be the first choice until now. The indexes are (1) life-extending effect, (2) the prevention to AIDS onset, and (3) reduction on number of cluster of differentiation (CD) 4 positive cells. Moreover, results on combination therapy between reverse transcriptase and a protease inhibitor were reported in succession. When a protease inhibitor was used in combination with two reverse transcriptase inhibitors (for example, AZT+ddI or AZT+3TC), it was found out that any protease inhibitor exhibited potent anti-viral activity. That is, the amount of viruses in blood was reduced to less than the detection limit in 60–90% of cases.

Thus, it is suggested that the amount of virus in the body might be reduced to a very low level by combination of plural anti-HIV agents, which effect at difference points through different mechanisms of action, and consequently, the onset of the disease could be prevented. However, the problems, such as the appearance of HIV-1 strains with multiple drug resistance and occurrence of some side effects by chronic administration, still remain to be solved. Moreover, although the proliferation of the virus is inhibited by the concomitant drug therapy, the viruses infected to the cells do not vanish completely. Recently, it was confirmed that HIV is produced in large quantities in a living body even under a prolonged latency period and the body repeats the immunologic elimination of the HIV, which leads to the aspect of the dynamic balance between the virus and the host. Therefore, in order to prevent the onset of AIDS, it is important to inhibit proliferation of the virus in the latency period and to suppress the level of the virus in blood to a low amount. Accordingly, in addition to the reverse transcriptase inhibitors and the protease inhibitors, development of an anti-HIV agent which acts through other mechanisms than conventional anti-HIV agents is desired. In concrete, such anti-HIV agent should act at its target other than the reverse transcriptases and the proteases utilized in the life cycles of HIV including an initial process of HIV infection.

HIV infection occurs by attachment of HIV to a host cell succeeded by entry of HIV into the host cell. The adhesion occurs through binding of glycoprotein120 (gp120), HIV envelop glycoprotein, and CD4, a receptor existing on the surface of the host cell. Therefore, a compound which inhibits binding of gp120 and CD4 is expected to inhibit attachment of HIV to the host cell, which enables protection from HIV infection. Then, an attempt to inhibit binding of gp120 and CD4 has been performed. For example, soluble CD4, prepared by genetic engineering technique, was administrated to the body on trial. Though inhibition activity was observed in vitro by the method described above, anti-HIV activity was not observed in vivo because of its short half life period. Moreover, it was revealed that infection did not occur when human CD4 was expressed in a mice cell, indicating existence of the second attachment molecule.

Recently, a series of results were reported that this second receptors belong to family of chemokine. HIV strains are divided roughly into two groups, one group contains strains exhibiting macrophage-tropic (M-tropic HIV) and another group contains strains exhibiting T cell-tropic (T-tropic HIV). It was suggested that the cell tropism observed between these virus strains is based on the difference in the molecular species of the second receptor. That is, it became clear that the type of HIV strains was determined by the type of the second receptor expressed on the target cells, namely CC chemokine receptor 5 (CCR5: M-tropic HIV receptor) or CXC chemokine receptor 4 (CXCR4: T-tropic HIV receptor). From these new knowledge, the manner of HIV adopted to invade into the target is hypothesized as follows at present. First, gp120 binds to CD4 and then the conjugate binds to CCR5 or CXCR4 expressed on the host cells. As the result, the structure of gp120 alters with denuding of glycoprotein41 (gp41). Then, it adheres and invades into a cell membrane which leads to formation of a giant cell (syncytium) and results in occurrence of infection. It was found that addition of the corresponding chemokine inhibited infection of HIV by competitive blockade of binding of HIV to the chemokine receptor on the cells. This series of discovery not only accelerated the elucidation on the mechanism of infection and onset of HIV, but also provided a novel viewpoint concerning anti-HIV strategy.

BRIEF SUMMARY OF INVENTION

To obtain a novel anti-HIV medicine which affects to such mechanism, the inventors have tried to obtain a compound that inhibits syncytium formation caused by fusion of HeLa cells expressing envelope glycoprotein (gp120 gp41) and HeLa cells expressing CD4 and CXCR4. The inventors have searched such compound in metabolic products of microorganisms. As the result, excellent HIV-inhibitory activity was found in the culture fluid of strain K97-0003, a newly isolated strain from soil. The strain is deposited to National Institute of Bioscience and Human-Technology, Agency of Industrial Science and Technology, MITI (1-1-3, Higashi, Tsukuba-shi, Ibaragi-ken, 305-8566, Japan) on Dec. 9, 1998, as strain K97-0003 (FERM BP-6670).

In the following, this invention is explained in detail. However, the detailed explanation of these preferred embodiments and examples are not intended to limit or restrict the range of the present invention.

DETAILED DESCRIPTION OF THE PREFERRED EMBODIMENTS

Figure 1:
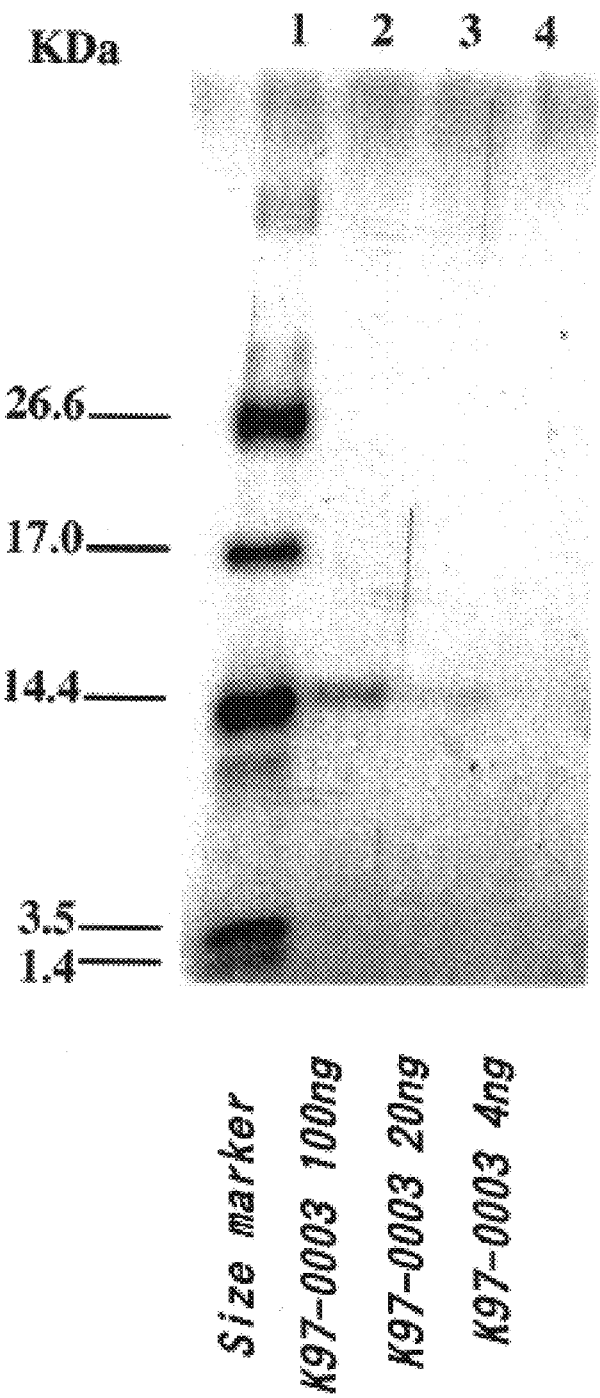
FIG. 1 is a photograph of SDS-polyacrylamide electrophoresis of K97-0003 peptide purified from strain K97-0003.

The inventors have isolated and purified a compound, that inhibits syncytium formation by fusion of HeLa cells expressing envelope glycoprotein and HeLa cells expressing CD4 and CXCR4 from culture fluid of K97-0003 strain. Consequently, the inventors obtained a polypeptide having the amino acid sequence of SEQ.ID.NO.1 in a sequence list. As this compound is novel, the inventors have designated it as K97-0003 peptide. The present invention was performed according to such knowledge and includes substantially the amino acid sequence of SEQ.ID.NO. 1 in a sequence list. Moreover, this invention provides K97-0003 peptide having anti-HIV activity by inhibiting fusion of the HeLa cells expressing envelope glycoprotein and the HeLa cells expressing CD4 and CXCR4. The amino acid sequence of SEQ.ID.NO. 1 corresponds to an amino acid sequence that is down stream from the 47th alanine in SEQ.ID.NO.2, the precursor peptide.

The present invention provides DNA coding for K97-0003 peptide including substantially the amino acid sequence shown in SEQ.ID.NO. 1. Such DNA includes a DNA containing the base sequence shown, for example, in SEQ.ID.NO. 3. The present invention further provides DNA coding for the precursor of K97-0003 peptide including substantially the amino acid sequence shown in SEQ.ID.NO. 2. Such DNA includes a DNA containing the base sequence shown, for example, in SEQ.ID.NO. 4. The present invention also provides strain K97-0003 which belongs to actinomycetes and having the ability to produce K97-0003 peptide. Furthermore, the present invention provides the method for preparing K97-0003 peptide characterized by culturing strain K97-0003 in a medium, accumulating K97-0003 peptide in the culture broth and obtaining K97-0003 peptide from said cultured broth.

Herein, the wording "substantial" means that one or more modifications, such as a substitution, addition, deletion, or insertion may occur in the amino acid sequence of said protein, so far as the K97-0003 peptide of the present invention has the biological activity of native activated form K97-0003 peptide. In particular, the K97-0003 peptide of the present invention has the activity to inhibit fusion of HeLa cells expressing envelope glycoprotein and HeLa cells expressing CD4 and CXCR4. It also means that modifications such as a substitution, addition, deletion, insertion, etc. of one or more codons corresponding to the modification of these amino acid sequences may occur in the base sequence of said gene, so far as the DNA according to the present invention retains the function to express said K97-0003 peptide. Therefore, for example, the peptide in which the sequence was deleted from the 1st (methionine) to the 46th (phenylalanine) of the amino acid sequence of K97-0003 peptide precursor (SEQ.ID.NO. 2) of the present invention is included in the modified amino acid sequence of this protein.

Accordingly, in the present invention, a polypeptide of K97-0003 peptide, a part of which is deleted, substituted by an amino acid sequence, or to which an amino acid sequence is added means the polypeptide for the amino acid sequence having at least 20%, preferably 30% and more preferably 50% of homology with the amino acid sequence of SEQ.ID.NO.1 in a sequence list. Similarly, a precursor polypeptide of K97-0003 peptide, a part of which is deleted, substituted by an amino acid sequence, or to which an amino acid sequence is added means the polypeptide for the amino acid sequence having at least 20%, preferably 30% and more preferably 50% of homology with the amino acid sequence of SEQ.ID.NO.2 in a sequence list.

Moreover, the gene that hybridizes with the base sequence of the gene coding for the amino acid sequence of K97-0003 peptide under a stringent condition means the gene for the base sequence having at least 20%, preferably 30% and more preferably 50% of homology with the base sequence of SEQ.ID.NO.3 in a sequence list. Similarly, the gene that hybridizes with the base sequence of the gene coding for the amino acid sequence of K97-0003 peptide precursor under a stringent condition means the gene for the base sequence having at least 20%, preferably 30% and more preferably 50% of homology with the base sequence of SEQ.ID.NO.4 in a sequence list.

In addition, the DNA according to the present invention includes the degenerate isomer coding for the same polypeptide which differs only in a degenerate codon, not only the base sequence encoding for the amino acid included in K97-0003 peptide according to the present invention. The activated-form K97-0003 peptide mentioned above means so-called mature form K97-0003 peptide. The K97-0003 peptide precursor means the peptide which has the signal peptide sequence region available for secretion of the peptide out of microorganism body, at the N terminal of so-called matured-form K97-0003 peptide.

A fragment of the polypeptide comprising the amino acid sequence of SEQ.ID.NO. 1 means at least 10 amino acids, and preferably at least 15 amino acids, for example, 20, 25, 30, 40, 50, and 60 amino acid portion of the polypeptide. The above-mentioned microorganism capable of producing the compound K97-0003 peptide, that inhibits fusion of HeLa cells expressing envelope and HeLa cells expressing CD4 and CXCR4, belongs to actinomycetes. It may be a microorganism without any particular limitation, so far as having the ability to produce said K97-0003 peptide compound. For example, strain K 97-0003 separated by the inventors is an example of such strain, which may be used the most effectively in the present invention, and the mycological properties of this strain is as follows.

Strain K97-0003 isolated by the inventors is the microorganism having the ability to produce K97-0003 peptide, and said strain exhibits following mycological properties. The vegetative hypha of said strain grows up moderately on oatmeal agar medium or nutrient agar medium, and the segmentation was observed. However, it does not grow in synthetic mediums, such as glucose and nitrate agar medium, or sucrose and nitrate agar medium. Although the aerial mycelium of said strain was not observed on almost all mediums, only on V8 juice agar medium of $1/10$ concentration, the aerial mycelium was slightly observed. In the observation under a microscope, the shape of the aerial mycelium is a straight line, and chains of 20 or more of spores were observed. The shape of the spore is cylindrical and the size is 1.0×0.5 $\mu$m. The surface of the spore is smooth and a sclerotium and a sporangium were not found out.

The cultural properties of the strain K97-0003, examined by E. B. Shirling-D. Gottlieb method (International Journal of Systematic Bacteriology, vol. 16, p.313, 1966) is shown in Table 1. The color tone was determined using Color Harmony Manual, the 4th edition (Container Corporation of America Chicago, 1958) as a standard color, and the code was described into the parenthesis, together with the color name. Unless otherwise specified, the detail data indicated below is the result of observation, performed on each medium at 27° C. after 2 weeks.

TABLE 1

| | | |
|---|---|---|
| Sucrose and nitrate agar | Growth | No growth |
| | Reverse | |
| | Aerial mycelium | |
| | Soluble pigment | |
| Glucose and asparagine agar (ISP) | Growth | Grows poorly, Pearl (2ba) |
| | Reverse | Yellow tint (1ba) |
| | Aerial mycelium | None |
| | Soluble pigment | None |
| Glycerol and asparagine agar (ISP) | Growth | Grows poorly, From cream to butter yellow (11/2ca–11/2ga) |
| | Reverse | From cream to light yellow (11/2ca–11/2ea) |
| | Aerial mycelium | None |
| | Soluble pigment | None |
| Starch and mineral salt agar (ISP) | Growth | No growth |
| | Reverse | |
| | Aerial mycelium | |
| | Soluble pigment | |
| Tyrosine agar | Growth | Grows poorly, Light ivory (2ca) |
| | Reverse | Cream (11/2ca) |
| | Aerial mycelium | None |
| | Soluble pigment | None |
| Oatmeal agar (ISP) | Growth | Grows moderately, Alabaster tint (13ba) |
| | Reverse | Blue tint (15ba) |
| | Aerial mycelium | None |
| | Soluble pigment | None |
| Yeast extract and malt extract agar (ISP) | Growth | Grows moderately, Light ivory (2ca) |
| | Reverse | Light white (2ea) |
| | Aerial mycelium | None |
| | Soluble pigment | None |
| Nutrient agar | Growth | Grows moderately, Light white (2ea) |
| | Reverse | Butter yellow (11/2ga) |
| | Aerial mycelium | None |
| | Soluble pigment | None |

TABLE 1-continued

| | | |
|---|---|---|
| Peptone, yeast extract and iron agar (ISP) | Growth | Grows moderately, Pearl pink (3ca) |
| | Reverse | Colonial blue (2ga) |
| | Aerial mycelium | None |
| | Soluble pigment | None |
| Glycerol and calcium malate agar | Growth | No growth |
| | Reverse | |
| | Aerial mycelium | |
| | Soluble pigment | |
| Glucose and peptone agar | Growth | No growth |
| | Reverse | |
| | Aerial mycelium | |
| | Soluble pigment | |
| 1/10 V8 juice agar | Growth | Grows poorly, Light ivory (2ca) |
| | Reverse | Light ivory (2ca) |
| | Aerial mycelium | White (a) |
| | Soluble pigment | None |

The physiological properties of strain K 97-0003 are as follows.
  (1) Formation of melanin pigment
    (i) Tyrosine agar Negative
    (ii) Peptone and yeast and iron agar Negative
    (iii) Glucose and peptone and gelatin agar Negative
    (iv) Trypton and yeast solution Negative
  (2) Tyrosinase reaction Negative
  (3) Production of hydrogen sulfide Negative
  (4) Reduction of nitrate Positive
  (5) Liquefaction of gelatin (21–23° C.) Positive
    (Glucose and peptone and gelatin medium)
  (6) Hydrolysis of starch No growth
  (7) Solidification (37° C.) of skimmilk Positive
  (8) Peptonization (37° C.) of skimmilk Positive
  (9) Growth temperature range 12–37° C.
  (10) Availability of Carbon Source (Priedhum-Gottlieb Agar medium)
Strain K 97-0003 utilizes glucose as carbon source. Said strain does not utilize arabinose, xylose, raffinose, melibiose, mannitol, fructose, rhamnose, inositol, and sucrose as carbon source.
  (11) Decomposition of Cellulose Negative
Briefly, the faxonomic properties on strain K 97-0003 is as follows. The diaminopimelic acid in the cell wall of said strain is meso form. As for the selectivity of the growth medium, although the vegetative hypha of said strain grows up well on oatmeal agar medium and nutrient agar medium and the fission was observed, it does not grow on synthetic mediums, such as glucose and nitrate agar, or sucrose and nitrate agar. On V8 sap agar medium of concentration of $1/10$, adhesion of the aerial hypha of above-mentioned strain was also found out slightly. The shape of the aerial hypha is a straight line and forms a long spore chain. The surface of the spore is smooth. As properties on culture, the vegetative hypha of said strain shows the color tone of beige, and the aerial hypha shows the color tone of white. From these results, it is estimated that said strain belongs to actinomycetes.

Although K97-0003 peptide-producing strain was explained above, the faxonomic properties of the above-mentioned strain is extremely easy to alter and not consistent, as general property observed in microorganisms. Said strain mutates naturally or by the artificial means for mutation, using ultraviolet irradiation or mutagens such as N-methyl-N'-nitro-N-nitrosoguanidine or ethyl methane sulfonate, etc. All the strains capable of producing K97-0003 peptide that belongs to actinomyces, including such artificial variants and natural variants, can be used for the present invention. The strains mutated by the cell technological procedures, such as cell fusion or genetic manipulation, are also included in the range of K97-0003 peptide-producing strains of the present invention.

For the culture method of K97-0003 peptide-producing strains of the present invention, a conventional method utilized the incubation of actinomycetes can be adopted. As for the culture medium, either a natural medium or a synthetic medium, containing catabolizable carbon source, nitrogen source, inorganic substance, etc. utilizable by a microorganism at a proper amount, can be used. As a carbon source, carbohydrates, such as glucose, mannose, maltose and molasses, organic acids, such as citric acid, malic acid, acetic acid and fumaric acid, alcohols, such as methanol and ethanol, hydrocarbons, such as methane, ethane, propane and n-paraffin, amino acids, such as glutamic acid, or glycerol can be used.

As for a nitrogen source, ammonium salts, such as ammonium chloride, ammonium sulfate, ammonium nitrate and ammonium phosphate, amino acids, such as aspartic acid, glutamine, cystine and alanine, urea, peptone, meat extract, yeast extract, dry yeasts, cone steep liquor, soybean flour, soluble vegetable protein, cottonseed oil, soybean casein, casamino acids, Pharmamedia, etc. can be used. As an inorganic substance, potassium monohydrogenphosphate, potassium dihydrogenphosphate, sodium dihydrogenphosphate, magnesium phosphate, magnesium sulfate, ferrous sulfate, manganese sulfate, copper sulfate, cobalt sulfate, zinc sulfate, calcium pantothenate, ammonium molybdate, aluminum potassium sulfate, barium carbonate, calcium carbonate, cobaltous chloride, salt, etc. can be used. In addition, compounds effective for promoting proliferation of said strain or production of K97-0003 peptide, microelements such as metal salt, vitamin, thiamin, etc., may be added to the medium if needed. Furthermore, when a specific compound is required for the growth of the microorganism, it is needed to add such compound to the medium. As for such compound, any compound useful for K97-0003 peptide production can be used, and all the compounds known to be used for cultivation of actinomycetes can be used.

The shaking culture, submerged culture with aerating and stirring, etc. using a liquid medium are preferable for large scale culture of K97-0003 peptide-producing strains. The incubation temperature can be set in the range that the K97-0003 peptide-producing strains can grow and produce K97-0003 peptide. According to the properties of K97-0003 peptide-producing strains, the incubation conditions can be selected property for performance of microbial incubation. When K97-0003 peptide, which is the cultured product, exists in the culture fluid, the culture fluid containing the microbial cells may also be obtained as the status, and used. However, generally, according to the conventional method, the filtrate of supernatant containing K97-0003 peptide can be used for isolation of the peptide after filtration or centrifugation of the cultured broth. When K97-0003 peptide exists in the body of microbial cells, K97-0003 peptide can be obtained by separating microbial cells from the cultured broth and collecting cells using means, such as a filtration or centrifugation, from the obtained cultured product. Subsequently, the cells were disrupted using a mechanical method, or an enzymatic method using lysozyme etc., and adding a chelating agent such as EDTA and /or a surfactant for solubilization of K97-0003 peptide, if needed.

The solution containing K97-0003 peptide thus obtained can be concentrated by reduced pressure concentration, membrane concentration or precipitated by salting-out using ammonium sulfate, or sodium sulfate, or by fractional precipitation using a hydrophilic organic solvent such as methanol, ethanol, acetone, etc. Then, the low molecular weight impurities can be removed by dissolving this precipitate in water and dialyzing it by a semi-permeable membrane. It can be also purified by an adsorbent, by gel filtration using a gel-filtration agent by adsorption chromatography, by ion exchange chromatography or by reversed phase chromatography. The K97-0003 peptide-containing solution obtained by these means can be further purified by treatments, such as vacuum concentration or lyophilization. The K97-0003 peptide may be a synthetic peptide.

EXAMPLES

The genetic manipulation using *Escherichia coli* was performed according to the method described in "Molecular Cloning" (Sambrook, J., Fritsch, E. F. and Maniatis, T., Cold Spring Harbor Laboratory Press, 1989). In the case of commercial kit, it was performed according to the operation procedures appended.

1. Cultivation of Strain K 97-0003

A loopful of mycelia of the K 97-0003 (FERM BP-6670) strain cultured on a slant agar medium was transferred, into a 500 ml of Erlenmeyer flask, containing a hundred ml of liquid medium (pH7.6) comprising 2.0% glucose, 0.4% polypeptone, 0.1% yeast extract, 0.4% meat extract and 0.25% sodium chloride. Then it was incubated with shaking for three days at 27° C. to obtain a seed culture solution. Subsequently, 2 ml of the seed culture solution was dispensed into 25 bottles of 500 ml Erlenmeyer flasks. Two hundreds ml of liquid medium (pH7.6), comprising 2.0% glucose, 0.4% polypeptone, 0.1% yeast extract, 0.4% meat extract and 0.25% sodium chloride, was dispensed into the flasks, respectively. They were incubated with shaking for three days at 27° C.

2. Purification of K97-0003 Peptide

The culture fluid was subjected to aspiratory filtration. Then the supernatant thus obtained was applied to DEAE-TOYOPEARL column (the diameter of 75 mm, the length of 250 mm, TOSOH Co.) and the effluent was collected. Then the effluent was applied to ODS column (the diameter of 50 mm, the length of 150 mm, Senshu Scientific Co., Ltd.), equilibrated with 10% acetonitrile aqueous solution prior to elution. The column was eluted with acetonitrile aqueous solution of stepwisely increased acetonitrile concentrations, in the order of 10% acetonitrile, 20% acetonitrile, 40% acetonitrile and 60% acetonitrile. The fractions having the activity to inhibit syncytium formation, by fusion of gp120-expressing HeLa cells and CD4 and CXCR4-expressing HeLa cells, were collected. Moreover, the acetonitrile in the fractions was removed by an evaporator. The assay of syncytium formation was performed by the below-mentioned method. This solution was applied to DEAE-TOYOPEARL column (the diameter of 50 mm, the length of 250 mm, TOSOH Co.) and eluted with 50 mM aqueous sodium chloride solution. The fractions with the inhibitory activity of syncytium formation were collected, and applied to ODS column (the diameter of 30 mm, the length of 100 mm, Sensyu Scientific Co., Ltd.) equilibrated with 5% acetonitrile aqueous solution prior to elution. It was eluted by linear gradient of 5% to 60% acetonitrile aqueous solution for 90 minutes at the flow rate of 2.5 ml/min and absorption at 225 nm was detected. The fractions having the activity were collected.

The fractions having the activity were collected, and the solvent in the fraction was removed by evaporator to obtain 50.1 mg of yellow crude compound. This compound was dissolved in 8 M aqueous urea solution, and the insoluble matter was removed by filtrating with a glass fiber filter (Whatman GF/C). Then distilled water was added to the filtrate thus obtained and the whole quantity was set to 4 ml. This solution was subjected to high performance liquid chromatography (SHISEIDO CAPCELLPAK C1 8 SG-120A, the inside-diameter of 20 mm×length of 250 mm, Shiseido Co., Ltd.) with separation of the solution into several aliquots. It was eluted by linear gradient of acetonitrile-0.01% TFA (1:9) to acetonitrile-0.01% TFA (45:55) for 40 minutes at the flow rate of 3.0 ml/min. The absorption was detected at 220 nm and the peak elute near 38 minutes was collected. The obtained fraction was subjected to vacuum concentration and 26.3 mg of K97-0003 peptide was obtained. The analysis of the obtained peptide on SDS polyacrylamide gel electrophoresis (SDS-PAGE) revealed that the molecular weight of the above-mentioned polypeptide was about 14 KDa (FIG. 1).

3. Determination of Amino Acid Sequence of K97-0003 Peptide

Figure 2:
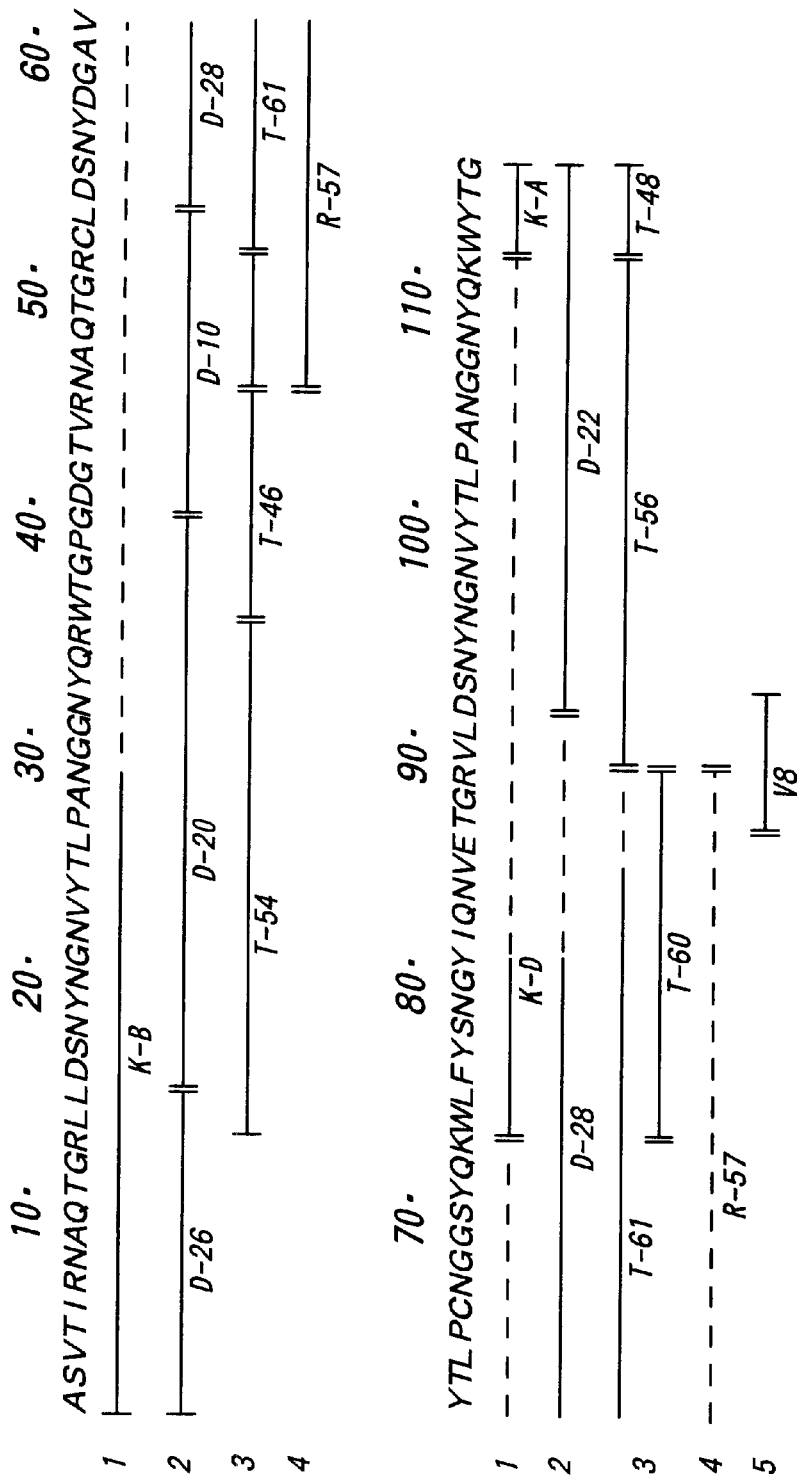
FIG. 2 is a drawing showing the amino acid sequences of K97-0003 peptide and the position of the peptide fragments used for sequence determination.

The primary structure of K97-0003 peptide was determined. The thiol groups of K97-0003 peptide were protected by reductive pyridyl ethylation and the peptide was digested with trypsin, arginyl endopeptidase, proteinase Lys-C and proteinase Asp-N, or endoproteinase Glu-C. The peptide fragments thus produced were analyzed by automatic Edman degradation (PPSQ-10 protein sequencer, SHIMAZU Co.). The N-terminal amino acid sequences of the each peptide obtained were connected to determine all of the amino acid sequences of K97-0003 peptide. The amino acid sequence of K97-0003 peptide is shown in SEQ.ID.NO. 1 of a sequence list. The amino acid sequence data base (PIR release 57, SWISSPROT release 37, PDB release 85, and DAD release 5) was searched and the sequence of said peptide was revealed to be novel. The sequences and the positions of the determined peptide fragments were shown in FIG. 2.

4. Cloning of the Gene Encoding K97-0003 Peptide

The following two sequences came into notice among the amino acid sequences of K97-0003 peptide, determined by the above-mentioned procedures. These are: (1) Ala-Ser-Val-Thr-Ile-Arg-Asn, which is the N-terminal sequence (SEQ ID NO.5) (amino acids corresponding to amino acid numbers of 1-7 in K97-0003 peptide) and (2) Gln-Lys-Trp-Tyr-Thr-Gly of the C-terminal sequence (SEQ ID NO.6) (amino acids corresponding to amino acid numbers of 109–114 of K97-0003 peptide). With reference to frequency of usage concerning codon of actinomycetes, the oligonucleotides of the following base sequences which corresponds to these amino acid sequences were synthesized by polymerase chain reaction (PCR).

That is, 5'-GCS TCS GTS ACS ATC CGS AAC-3' was synthesized as a sense primer (SEQ ID NO.7) and 5'-CC SGT GTA CCA CTT CTG-3' was synthesized as an anti-sense primer (SEQ ID NO.8), respectively. As the result of PCR using chromosomal DNA of strain K 97-0003 as a template and the two oligonucleotides mentioned above as primers, an amplified DNA fragment of about 300 pb was recognized. The amplified fragment was recovered and ligated to T cloning site of T cloning vector pCR2.1 (Invitrogen Co.) using DNA ligation kit version 2 (Takara Shuzo Co., Ltd.). *Escherichia coli* inv α F' (Invitrogen Co.) was transformed in the ligation solution and then the recombinant plasmid was extracted from the colonies observed on the ampicillin-containing Luria-Bertani (LB) agar medium. As the result of analysis on the base sequence inserted into the recombinant plasmid, complete agreement was recognized with the base sequence encoding for amino acid sequence of K97-0003 peptide. Accordingly, it was concluded that this DNA fragment was a part of gene encoding for K97-0003 peptide. part of gene coding for K97-0003 peptide.

Chromosomal DNA of strain K97-0003 was partially digested with restriction enzyme MboI to obtain a fragment of about 40 kb. This DNA fragment was ligated to cosmid vector pWE15 (Stratagene Co., U.S.) digested by restriction enzyme BamHI, and packaged into phage particles using Read.To.Go Lambda Packaging Kit (Amersham Pharmacia Biotech Co.).

The obtained phage particle was infected with *Escherichia coli* XL-1 blue MR (Stratagene Co., U.S.) according to the conventional method. On LB agar medium containing ampicillin, the phage solution was inoculated so as that about 1,000 colonies of *Escherichia coli* might emerge on a petri plate with a diameter of 9 cm, and incubated at 30° C. over night. Furthermore, Highbond N+(Pharmacia Biotech Co.) was placed on new LB agar medium containing ampicillin (final concentration of 100 µg/ml), colonies were transferred on the nylon film according to the conventional method and incubated at 30° C. over night. The colony hybridization was performed on the colonies grown on the nylon film. The digoxigenin labeled DNA fragment used as a probe was prepared by PCR DIG probe synthesis kit (Boeringer mannheim Co.). At the preparation of the labeled DNA fragment, the cloned DNA containing the DNA fragment of 300bp described above encoding for K97-0003 peptide was used as a templete and following two synthetic oligonucleotides, which was designed newly for this purpose, were used as primers. That is, 5'-GCC TCG GTG ACC ATC CGC-3' corresponding to the base numbers 1-18 of SEQ. ID. NO.2 in a sequence list was used as the sense primer (SEQ ID NO.9) and 5'-T GTC GAG CAC GCG TCC-3' corresponding to the complemental sequence of base numbers 258–274 of SEQ ID. NO.2 in a sequence list was used as the anti-sense primer (SEQ ID NO.10), respectively. The hybridization and the detection of positive clones were performed using DIG nucleic acid detecting kit (Boeringer mannheim Co.).

Figure 3:
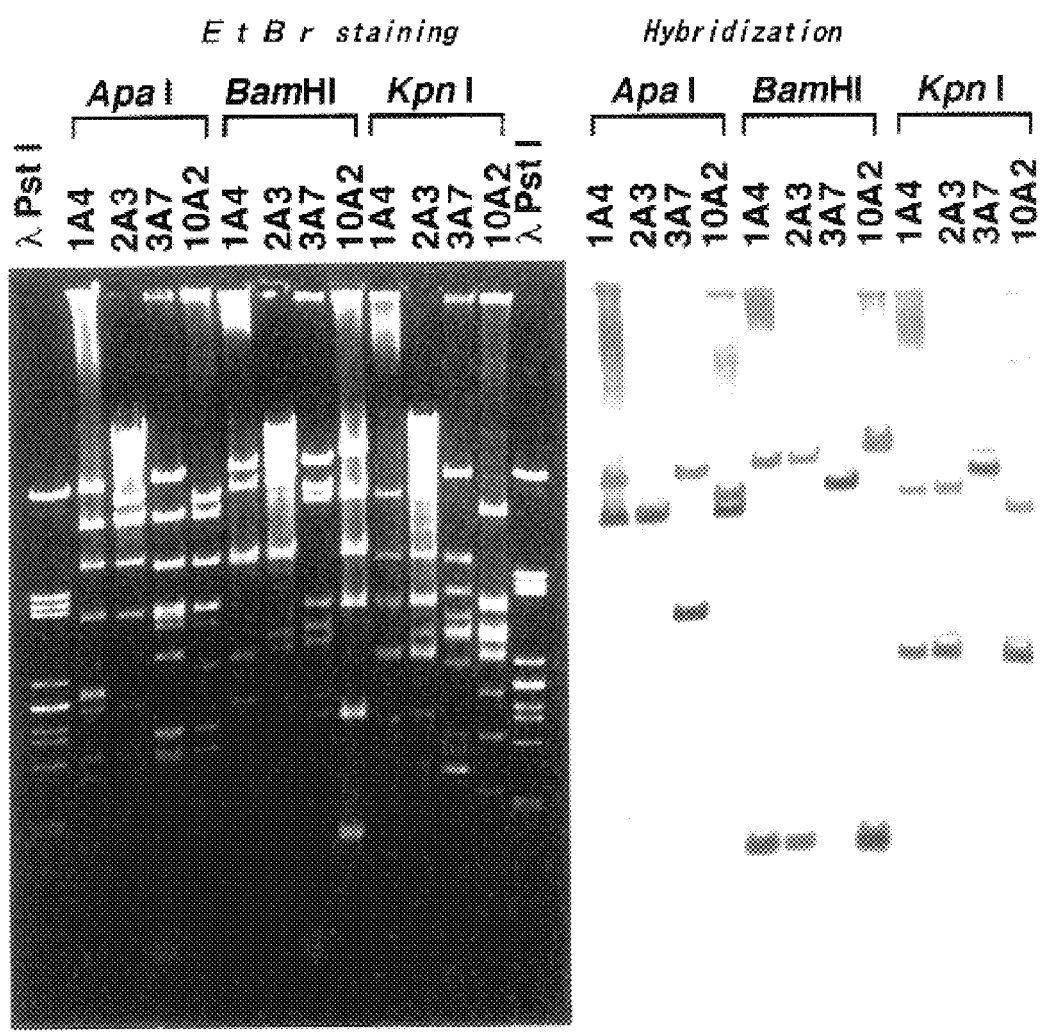
FIG. 3 is a photograph of Southern hybridization showing the existence of cloned K97-0003 peptide gene.

As the result, seven positive clones were obtained from about 10,000 colonies. Plasmid was recovered from the positive clones, and digested by restriction enzymes ApaI, BamHI, and KpnI independently and separated by 0.8% agarose gel electrophoresis. The separated DNA was transferred from the gel to the nylon film and fixed, then subjected to Southern hybridization using the above-mentioned probe. An ApaI fragment of about 7 bp, a BamHI fragment of about 800 bp and a KpnI fragment of about 3 kb, were found out as DNA fragments which hybridizes with the probe. These fragments were obtained from three clones designated as 1A4, 2A 3 and 10A2, respectively. Among positive clones, the results of Southern hybridization on 1A4, 2A3, 3A7, and 10A2 were shown in FIG. 3. Then the plasmids of positive clones were digested with restriction enzyme KpnI, and fractionated by 1.0% agarose gel electrophoresis.

Figure 4:
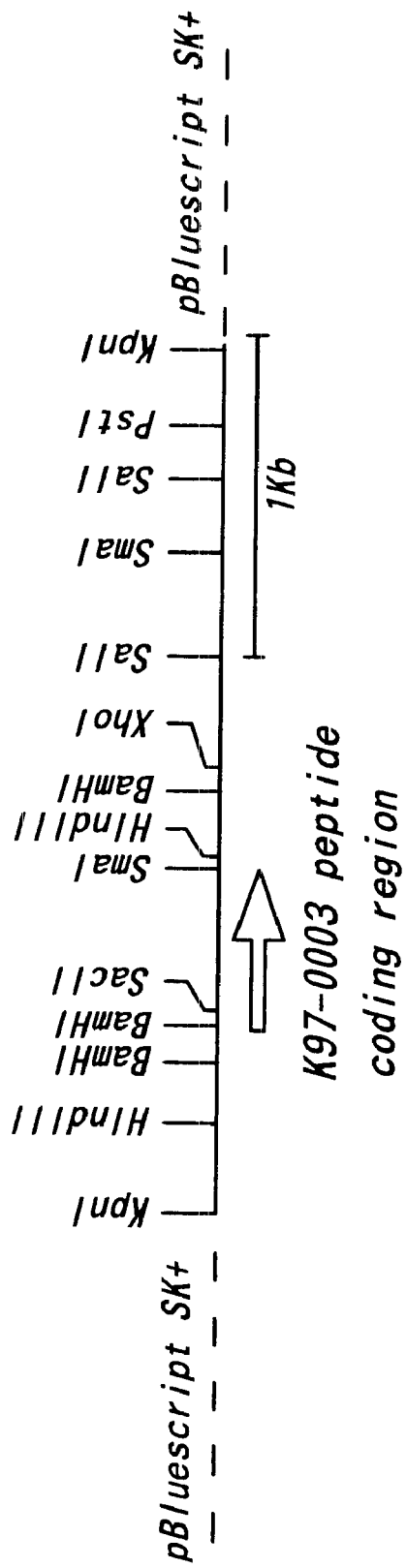
FIG. 4 is a restriction enzyme map of the DNA fragment of about 3 kb containing K97-0003 peptide gene derived from strain K97-0003, and the drawing showing the position and the direction of the K97-0003 peptide gene.

KpnI fragment of about 3 kb was recovered using EASYTRAP Ver.2 (Takara Shuzo Co., Ltd.), and it was ligated to pBluescriptIISK+ digested with KpnI. Then it was used to transform *Escherichia coli* JM109. Plasmid was recovered from subclone thus obtained and the restriction enzyme map of the inserted DNA fragment was prepared. The restriction enzyme map prepared is shown in FIG. 4. Moreover, the DNA fragments obtained by digesting the subclone with various restriction enzymes were analyzed by Southern hybridization. As the result, the fragment containing K97-0003 peptide gene was limited to about 600 bp ranging to BamHI site to SmaI site (the bar represented in FIG. 4). The several restriction enzyme fragments containing this region were subcloned to pBluescriptIISK+, and the base sequence of the obtained recombinant plasmids were analyzed.

PCR was performed by Thermo sequenase TM cycle sequencing kit (SHIMAZU Co.), using said subclones as a template according to the appended operation method. Sequencing of the base was performed by the automatic fluorescent DNA sequencer DSQ2000. Data on base sequence was edited into a continuous base sequence using DNA base sequence-linked program of GENETYX. Consequently, the base sequence (SEQ.ID.NO. 4) coding for the precursor peptide of K97-0003 peptide (SEQ.ID.NO. 1) was obtained. The precursor of K97-0003 peptide means, as mentioned above, the peptide having the sequence region of the signal peptide, used for secretion out of a microorganism, in the N-terminal of K97-0003 peptide. The base sequence data (SEQ.ID.NO. 4) of the precursor peptide thus obtained was translated to its corresponding amino acid sequence, which provides amino acid sequence (SEQ.ID.NO. 2) of K97-0003 peptide precursor. The base sequence coding for K97-0003 peptide is further shown in SEQ.ID.NO.3 in a sequence list.

5. Measurement of Syncytium Formation

50 μl of HeLa/CD4 /LTR cell suspension prepared to $1.6 \times 10^5$ cells/ml was inoculated into every each well of 96 well plate (IWAKI MICROPLATE 96well), and 10 μl of the sample, diluted in a series of concentration with phosphate buffer physiological saline, was added to every each well. Then, 50 μl of HeLa135/env(envelope glycoprotein: originated from T-tropic HIV-1)/Tat cell suspension prepared to $1.6 \times 10^5$ cells/ml was dispensed to every well, and incubated in an incubator at 37° C. under 5% $CO_2$ air current for 24 hours. After removal of the culture fluid from each well, 20 μl of cell lysis solution was added to every each well, and the plate was left at the room temperature for about 10 minutes.

Continuously, 100 μl of chromogenic substrate solution (Z-buffer: 80 μl+4 mg/ml o-nitrophenyl-β-D-glactopyranoside:20 μl) was added to each well, and reacted in the incubator at 37° C. Z-buffer is composed of 60 mM disodium hydrogenphosphate, 40 mM sodium dihydrogenphosphate, 20 mM potassium chloride, 1 mM magnesium sulfate, and 5 mM β-mercaptoethanol, with its pH of 7.0. After 80 minutes, 25 μl of reaction stop solution (2M $Na_2CO_3$) was added to it, and the absorbance at 405 nm was measured using colorimeter (Organ ON SystemMicrowell System Reader 510). Syncytium formation ability was calculated from the obtained absorbance by the following formula.

Syncytium formation ability=the absorbance of the well with sample addition/absorbance of control×100

Peptide concentration ($IC_{50}$) which inhibits 50% of syncytium formation ability thus obtained is shown in the following table 2.

6. Measurement of Anti-HIV Activity by Suppression of Cytopathic Effect

Anti-HIV activity was measured from suppression of cytopathic effect caused by HIV infection. The HIV infected MT-4 cell ($2.5 \times 10^4$ cells/well, degree of multiple infection: 0.01) was added to 96 well titer plate immediately after infection. At the same time, K97-0003 peptide of various concentration was also added to the plate. In order to examine cytopathic effect of K97-0003 peptide on MT-4 cell, cells uninfected by HIV was incubated with K97-0003 peptide of various concentrations in the same manner. After five days of incubation at 37° C. in a $CO_2$ incubator, the number of cell survived was measured by MTT method.

The biological activity of K97-0003 peptide evaluated by the method described above is shown in Table 2 by comparison with chloropeptin, a HIV inhibitor originated from Streptomyces sp. strain WK-3419. As well, chloropeptin is known to exhibit anti-HIV activity by inhibition of gp120-CD4 binding. The cytopathic effect is shown by the following value in Table 2.

(1) $EC_{50}$: It is the concentration of K97-0003 peptide which inhibits 50% of the cytotoxicity by HIV infection, and is the parameter of anti-HIV activity of the peptide.

(2) $CC_{50}$: It is the concentration of K97-0003 peptide that causes cytotoxicity to 50% of cells, and is the parameter of cytotoxic effect of the peptide.

(3) SI (Selectivity Index): It is an effectiveness factor and calculated by $CC_{50}/EC_{50}$.

As shown in Table 2, K97-0003 peptide inhibited syncytium formation at low-concentration (60 nM), and exhibited anti-HIV activity ($EC_{50}$: 230 nM). Moreover, significant cytotoxicity was ($CC_{50}$:>8 μM) not observed at concentration that exhibits anti-HIV activity. The effectiveness of K97-0003 peptide was confirmed from the result described above.

TABLE 2

|  | K97-0003 peptide | Chloropeptine |
|---|---|---|
| $IC_{50}$ of syncytium formation ability | 60 nM (0.8 μg/ml) | 0.5 μM (1.7 μg/ml) |
| $BC_{50}$ | 230 nM | 1.6 μM |
| $CC_{50}$ | >8 μM | >600 μM |
| SI | >35 | >375 |

7. Measurement of Anti-HIV Activity by MAGI Assay

Furthermore, the anti-HIV activity of K97-0003 peptide was measured by MAGI assay (The multinuclear activation of a galactosidase indicator), which can evaluate activation of a gene using β-galactosidase activity as an indicator. The cells were transformed by CD4 gene and CCR5 gene, the coreceptor of HIV. Moreover, LTR (long terminal repeat) of HIV and β-galactosidase gene were further introduced into the transformed cells. Such cells were used for this assay. In such cells, β-galactosidase is activated accompanied with HIV infection of the cell. Therefore, infection of HIV can be measured by color development of X-gal (5-bromo-4-chloro-3-indolyl-β-galactoside), which is the substrate of β-galactosidase. MAGI assay was performed according to the method of R. Arakaki et al. (R. Arakaki et al., Jounal of Virology, Vol.73, No.2, p1719–1723) and the method of J. Kimpton et al. (J. Kimpton et al., Jounal of Virology, Vol.66, No.4, p2232–2239). The infection inhibitory activity of K97-0003 polypeptide on various HIV is shown in Table 3.

TABLE 3

|  | HIV | Infection preventive activity ($IC_{50}$nM) |
|---|---|---|
| T-tropic HIV | III B | 2.0 |
|  | O18A | 110 |
|  | NL4-3 | 16 |
| M-tropic HIV | JR-CFS | 38 |
| HIV-2 | ROD | 14 |
|  | EHO | 3.7 |

In Table 3, K97-0003 polypeptide exhibited $IC_{50}$ value of nM order to both T-tropic HIV and M-tropic HIV. The K97-0003 polypeptide also exhibited infection inhibitory activity to HIV-2. This result shows that K97-0003 polypeptide has the inhibitory activity on HIV infection, with the result of Table 2.

K97-0003 peptide of the present invention inhibited syncytium formation by fusion of HeLa cells expressing T-tropic envelope glycoprotein and HeLa cells expressing CD4 and CXCR4, and exhibited anti-HIV activity. The peptide exhibited inhibitory activity on not only infection of T-tropic HIV but also that of M-tropic HIV. Therefore, the present invention provided a polypeptide efficient as a prophylactic and therapeutic medicine of AIDS. Furthermore, the gene encoding for K97-0003 peptide of the present invention is available for production of recombinant K97-0003 peptide. The recombinant peptide can be used as a prophylactic and therapeutic medicine of AIDS, as the same as the native K97-0003 peptide.

What is claimed is:

1. An isolated polypeptide comprising an amino acid sequence shown in following (a) or (b);
   (a) a polypeptide referred to as amino acid numbers from 1 to 114 in SEQ.ID.NO. 1 in a sequence list;
   (b) the polypeptide (a), a part of which is deleted, substituted by an amino acid sequence, and/or to which amino acid sequence is added, having inhibitory activity on syncytium formation.

2. An Actinomycete strain FERM BP-6670 that produces the polypeptide according to claim 1.

3. An isolated gene coding for the polypeptide according to claim 1.

4. An isolated gene comprising a base sequence shown in following
   (c) or (d) encoding the polypeptide according to claim 1;
   (c) a gene referred to as base numbers from 1 to 342 in SEQ.ID.NO. 3 in a sequence list;
   (d) a gene that hybridizes with the base sequence (c) under stringent conditions, that encodes for a polypeptide having inhibitory activity on syncytium formation.

5. An isolated fragment of the polypeptide according to claim 1, having inhibitory activity on syncytium formation.

6. A method of producing a polypeptide comprising the steps of: (1) culturing actinomycete strain FERM BP-6670 to produce a culture product, wherein said culture product comprises the polypeptide of claim 1, and (2) extracting said polypeptide from said culture product.

7. An isolated precursor polypeptide which is a precursor of the polypeptide according to claim 1, said precursor polypeptide comprising amino acid numbers from 1 to 160 in SEQ ID NO.2 in a sequence list.

8. An isolated gene coding for the precursor polypeptide according to claim 7.

9. An isolated gene comprising a base sequence shown in following (g) or (h) encoding the precursor polypeptide according to claim 7;
   (g) a gene referred to as base numbers from 1 to 480 in SEQ.ID.NO. 4 in a sequence list;
   (h) a gene that hybridizes with the base sequence (g) under stringent conditions, and encodes for a precursor polypeptide which is a precursor of the polypeptide according to claim 1, said polypeptide having inhibitory activity on synctium formation.

* * * * *